US012763191B2

(12) United States Patent
Narvaez

(10) Patent No.: US 12,763,191 B2
(45) Date of Patent: Oct. 13, 2026

(54) UTILIZING MULTI-LAYER CACHING SYSTEMS FOR STORING AND DELIVERING IMAGES

(71) Applicant: CERNER INNOVATION, INC., Kansas City, KS (US)

(72) Inventor: Juan David Narvaez, Kansas City, KS (US)

(73) Assignee: CERNER INNOVATION, INC., Kansas City, MO (US)

( * ) Notice: Subject to any disclaimer, the term of this patent is extended or adjusted under 35 U.S.C. 154(b) by 1204 days.

(21) Appl. No.: 17/110,671

(22) Filed: Dec. 3, 2020

(65) Prior Publication Data

US 2022/0181005 A1 Jun. 9, 2022

(51) Int. Cl.

*G16H 30/20* (2018.01)
*G06F 12/0802* (2016.01)
*G06F 16/53* (2019.01)

(52) U.S. Cl.

CPC ......... *G16H 30/20* (2018.01); *G06F 12/0802* (2013.01); *G06F 16/53* (2019.01); *G06F 2212/60* (2013.01)

(58) Field of Classification Search

USPC .............................................................. 705/2
See application file for complete search history.

(56) References Cited

U.S. PATENT DOCUMENTS

| | | | | |
|---|---|---|---|---|
| 10,790,056 B1 * | 9/2020 | Accomazzi | G16H 30/20 |
| 2010/0074484 A1 * | 3/2010 | Ohkubo | G06F 16/50 382/128 |
| 2020/0293497 A1 * | 9/2020 | Wu | G06N 3/047 |
| 2021/0157743 A1 * | 5/2021 | Chandrasekaran | G06N 3/044 |
| 2022/0044395 A1 * | 2/2022 | Ebrahimi | G06F 16/58 |

OTHER PUBLICATIONS

Gerek, Ö. N. (1993). Design and implementation of a PC based medical image workstation (Order No. 29046589). Available from ProQuest Dissertations and Theses Professional. (2652593263). Retrieved from https://dialog.proquest.com/professional/docview/2652593263?accountid=131444 (Year: 1993).*

* cited by examiner

*Primary Examiner* — Bennett Stephen Erickson
(74) *Attorney, Agent, or Firm* — Kraguljac Law Group LLC

(57) ABSTRACT

Methods, systems, and computer-storage media are provided for utilizing a multi-layer caching system to provide fast and accurate diagnostic image renderings to a healthcare provider. After receiving a request to view medical image data that comprises at least one image frame, the system accesses a least recently used (LRU) memory cache and a local database to determine whether the requested medical image data is stored locally. If the medical image data is not stored locally, the system accesses a remote image storage and retrieves the medical image data requested. The medical image data is then transformed from a compressed format to a decompressed format and transmitted to a user for review. Additionally, the decompressed medical image data is stored locally at either the LRU memory cache or the local database until no longer needed.

20 Claims, 6 Drawing Sheets

UTILIZING MULTI-LAYER CACHING SYSTEMS FOR STORING AND DELIVERING IMAGES

BACKGROUND

Over the years, the cost of healthcare has increased significantly and the management of individual healthcare has become more complex. In the course of treating individuals for various healthcare problems, healthcare providers frequently order radiological examinations for diagnostic and treatment purposes. The images generated from such an exam can vary in size and detail depending on the type of exam. Once the images are generated they may be saved to either local or remote storage locations within a healthcare system's network. A healthcare system treating thousands of individuals will have several thousands of medical images to be stored. As one can imagine, storing medical images takes up significant resources and space. In order to manage the burden on a system, such medical images may be stored in a variety of formats and locations both locally and remotely.

Once a radiological exam, such as an x-ray or CT scan, is conducted, various healthcare providers, including but not limited to a radiologist will review the images generated from the radiological exam. When a radiologist receives a request to review a medical image generated by the radiological exam, the radiologist initiates a request to the healthcare system to view the images. When this request is made, the process of locating, retrieving, and displaying the images for the radiologist consists of multiple steps. Because files storing the medical images requested may be very large and may be stored in a variety of locations, the healthcare system may utilize significant resources and time in obtaining, downloading, processing, and generating the requested medical images for viewing. Additionally, because medical image data may contain thousands of image frames and therefore take up large amounts of space, each medical image data file may be processed to compress the medical image data in order to order to store the data effective. The system may conduct various processes on the data in order to more effectively store the data without exhausting system resources and storage when not in use. As such, the process of communicating within the system to locate the requested medical images and data, retrieve the medical image data from its storage location, transform the medical image data into a usable format, and generate the images requested for review can be costly and time consuming.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

When a radiological exam, such as an x-ray or CT scan, is conducted, various healthcare providers, including but not limited to a radiologist will review the images generated from the radiological exam. When a radiologist receives a request to review a medical image generated by the radiological exam, the radiologist initiates a request to the healthcare system to view the images. When this request is made, the process of locating, retrieving, and displaying the images for the radiologist consists of multiple steps. Because files storing the medical images requested may be very large and may be stored in a variety of locations, the healthcare system may utilize significant resources and time in obtaining, downloading, processing, and generating the requested medical images for viewing. Additionally, because medical image data may contain thousands of image frames and therefore take up large amounts of space, each medical image data file may be processed to compress the medical image data in order to order to store the data effectively. The system may conduct various processes on the data in order to more effectively store the data without exhausting system resources and storage when not in use. As such, the process of communicating within the system to locate the requested medical images and data, retrieve the medical image data from its storage location, transform the medical image data into a usable format, and generate the images requested for review can be costly and time consuming.

Various types of radiological exams are a critical and regular component of managing the healthcare of an individual. Radiological exams are used to diagnose the cause of symptoms presented, monitor how an individual's body is responding to treatment, and screen for different illnesses such as cancer or heart disease. As technology has progressed over the years, there are numerous types of radiological exams available for a variety of needs. Some examples of common radiological examinations utilized regularly are x-rays, magnetic resonance imaging (MRIs), computed tomography scan (CT or CAT scan), fluoroscopy, mammography, nuclear medicine (e.g. bone scans), positron emission tomography (PET scan), and ultrasounds. Each type of radiological exam is composed of image data which can include as little as one image frame to as many as hundreds or thousands of image frames. For example, a simple x-ray of the ankle may include a single image frame while a CT scan of the brain can include hundreds of image frames with intricate detailing that are compiled together in multiple series for review. As such, the amount of image data and size of a file corresponding to the image data can vary from very small to very large. Consequently, medical images require significant resources to store and manage them.

In many instances, a healthcare system stores medical image data associated with radiological images remotely, such as in a cloud computing environment, due to their size and to maintain efficiency and manage burden on local systems. Therefore, when a healthcare provider requests to view, for example, a CT scan, the system may go through various processes and communications pathways in order to locate, access, retrieve, and process the requested images prior to being able to display the images of the CT scan for review. The amount of time from requesting the image to displaying the image will vary depending on the size of the medical image and the location where the medical image is stored. To store image data more efficiently, many systems may transform the image data from a radiological exam to compressed data or decompressed data. As such, each time an image is requested, the system may additionally have to transform data into a viewable format from the format the image data has been stored in. For example, if the medical image data is stored remotely, it will likely be in a compressed format and therefore require decompression prior to being able to be transmitted for viewing. Often times, when a healthcare provider is requesting such data, time may be of essence. Therefore, a system in which the medical image data can be more effectively stored and then located and transmitted for viewing may be critical for managing the medical care of an individual. The ability to deliver timely and provide efficient access to images, interpretations, and related data could make the difference between life or death.

For example, with ultrasounds, the display frame rate may be paramount to accurate diagnosis as the clinician must be able to see an accurate reproduction of the motion captured from the exam, which means that the displaying system must be able to render frames as fast as possible such that an accurate reproduction is achieved.

Additionally, because the medical image data for each image may require various processing, it is beneficial to store such image data in the most efficient way for quick access and retrieval for future use. Historically, each time an image was requested, the system would have to communicate with a remote storage source to locate, access, retrieve, process, and generate the image for review on the user's screen. However, it would be beneficial to have a system in which the image data is stored in a more efficient format such that the process of locating, accessing, retrieving, processing, and generating the image for review on the user's screen is faster, and more efficient. For example, by storing certain image data locally and in a usable format, the image data can be transmitted for viewing without further processing and faster than before.

The challenges presented by the current methods of storing image data and transmitting it upon request are addressed by the present disclosure. At a high level, the present disclosure discloses a dynamic multi-layer caching system useful for providing fast diagnostic image renderings to a healthcare provider for viewing one or more medical images, such as a CT scan. The system allows a user, via a request to view an image, to use one process in order to locate, access, process, and transmit the image requested for viewing, regardless of whether the image requested is stored locally or remotely. The system may store the image data for the requested image in a format in which the data is decompressed once requested for future use, eliminating the need for decompression of data each time the image is requested. The system can also store the decompressed data locally. As such, the system improves the processing time, reduces the resources needed, and provides more efficient viewing of images.

Aspects herein describe computer-storage media, computerized methods, and computing systems that allow healthcare providers, such as radiologists, to quickly view requested medical images. The system comprises receiving a request to view a medical image. Each medical image comprises medical image data that includes at least one image frame. The system then accesses local storage, such as a least recently used memory (LRU) cache to determine whether the requested medical image data is stored in the LRU memory cache. Upon determining the medical image data is not stored in the LRU memory cache, the system accesses a local database to determine if the medical image data requested is stored in it. If it is determined that the requested medical data is also not stored in the local database, the system then accesses a remote image storage and locates the medical image data for the requested medical image. The medical image data is retrieved from the remote image storage and the system may perform processing steps such as separating the medical image data into pixel data and metadata for each image frame. Then, the system may decompress the pixel data and metadata for each image frame for future use. The decompressed medical image data may remain stored locally at the LRU memory cache or local database for future use until the system determines that the medical image data is no longer needed. Once processed, the system transmits the requested medical image, including the corresponding medical image data to the healthcare provider for review.

As well, aspects herein are also directed to a dynamic system useful for providing fast diagnostic image renderings to a healthcare provider for viewing one or more medical images comprising a LRU memory cache, a local database, a remote image storage, and one or more processors. The system also includes a storage storing a computer program product comprising computer instructions that, upon execution by the one or more processors, cause the one or more processors to perform operations comprising receiving a first request from a first user using an image viewing application for a first medical image comprising medical image data. The system then accesses the LRU memory cache, database, and remote image storage to determine the location of the medical image data. If the medical image data is located locally at the LRU memory cache or local database, the system will transmit the medical image with its corresponding medical image data to the user for viewing. When the system determines that the medical image data is stored in the remote image store, the system retrieves the medical image data for the first medical image from the remote image store in a compressed format. The system decompresses the medical image data for storage locally at either the LRU memory cache or local database for future use. By decompressing the data, the system minimizes the processing needed on the medical image data to respond to the next request to view the medical image data, thereby making the process faster, more efficient. The system also transmits the first medical image to the first user for viewing. Additionally, the system receives a second request to view the first medical image. Because the medical image data has already been processed, decompressed, and stored locally, the system is able to retrieve the medical image data from either the LRU memory cache or the local database without further reprocessing. In this case, the system is able to retrieve the medical image data stored locally much faster than when the medical image data was stored remotely or locally in its original format. The medical image data is also transmitted for viewing, thereby satisfying the second request in a faster, more efficient manner.

BRIEF DESCRIPTION OF THE DRAWINGS

Embodiments are described in detail below with reference to the attached drawings figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As used herein, the term facility, may be any facility which provides healthcare to an individual such as, but not limited to, a hospital, acute care facility, rehabilitation facility, urgent care facilities and the like.

Figure 1:
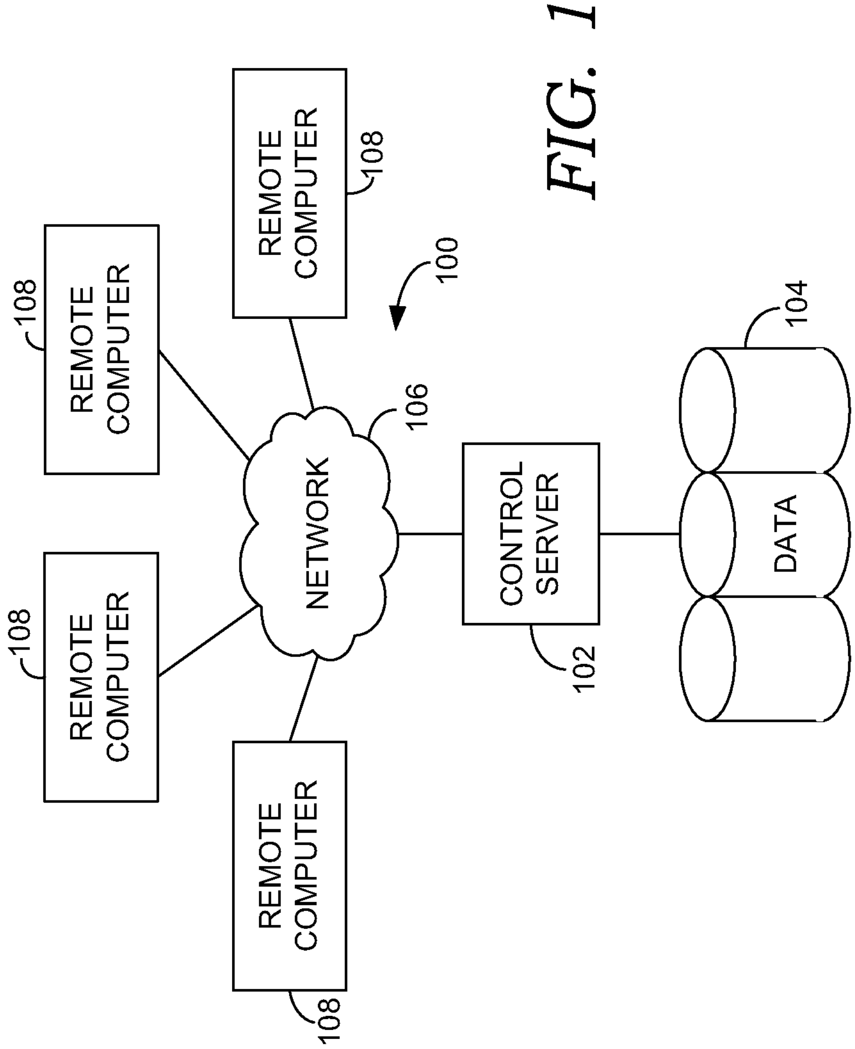
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein. It will be appreciated by those having ordinary skill in the art that the connections illustrated in FIG. 1 are also exemplary as other methods, hardware, software, and devices for establishing a communications link between the components, devices, systems, and entities, as shown in FIG. 1, may be utilized in the implementation of the present invention. Although the connections are depicted using one or more solid lines, it will be understood by those having ordinary skill in the art that the exemplary connections of FIG. 1 may be hardwired or wireless, and may use intermediary components that have been omitted or not included in FIG. 1 for simplicity's sake. As such, the absence of components from FIG. 1 should not be interpreted as limiting the present invention to exclude additional components and combination(s) of components. Moreover, though devices and components are represented in FIG. 1 as singular devices and components, it will be appreciated that some embodiments may include a plurality of the devices and components such that FIG. 1 should not be considered as limiting the number of a device or component.

The present technology might be operational with numerous other special-purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be operational and/or implemented across computing system environments such as a distributed or wireless "cloud" system. Cloud-based computing systems include a model of networked enterprise storage where data is stored in virtualized storage pools. The cloud-based networked enterprise storage may be public, private, or hosted by a third party. In some embodiments, computer programs or software (e.g., applications) are stored in the cloud and executed in the cloud. Generally, computing devices may access the cloud over a wireless network and any information stored in the cloud or computer programs run from the cloud. Accordingly, a cloud-based computing system may be distributed across multiple physical locations.

The present technology might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer-readable media does not include signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations including operating systems, device drivers and medical information workflows. The remote computers might also be physically located in traditional and nontraditional medical/healthcare care environments so that the entire medical community might be capable of integration on the network. The remote computers might be personal computers, servers, routers, network PCs, peer devices, other common network nodes, or the like and might comprise some or all of the elements described above in relation to the control server. The devices can be personal digital assistants or other like devices. Further, remote computers may be located in a variety of locations including in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Health care providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire medical community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote medical device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
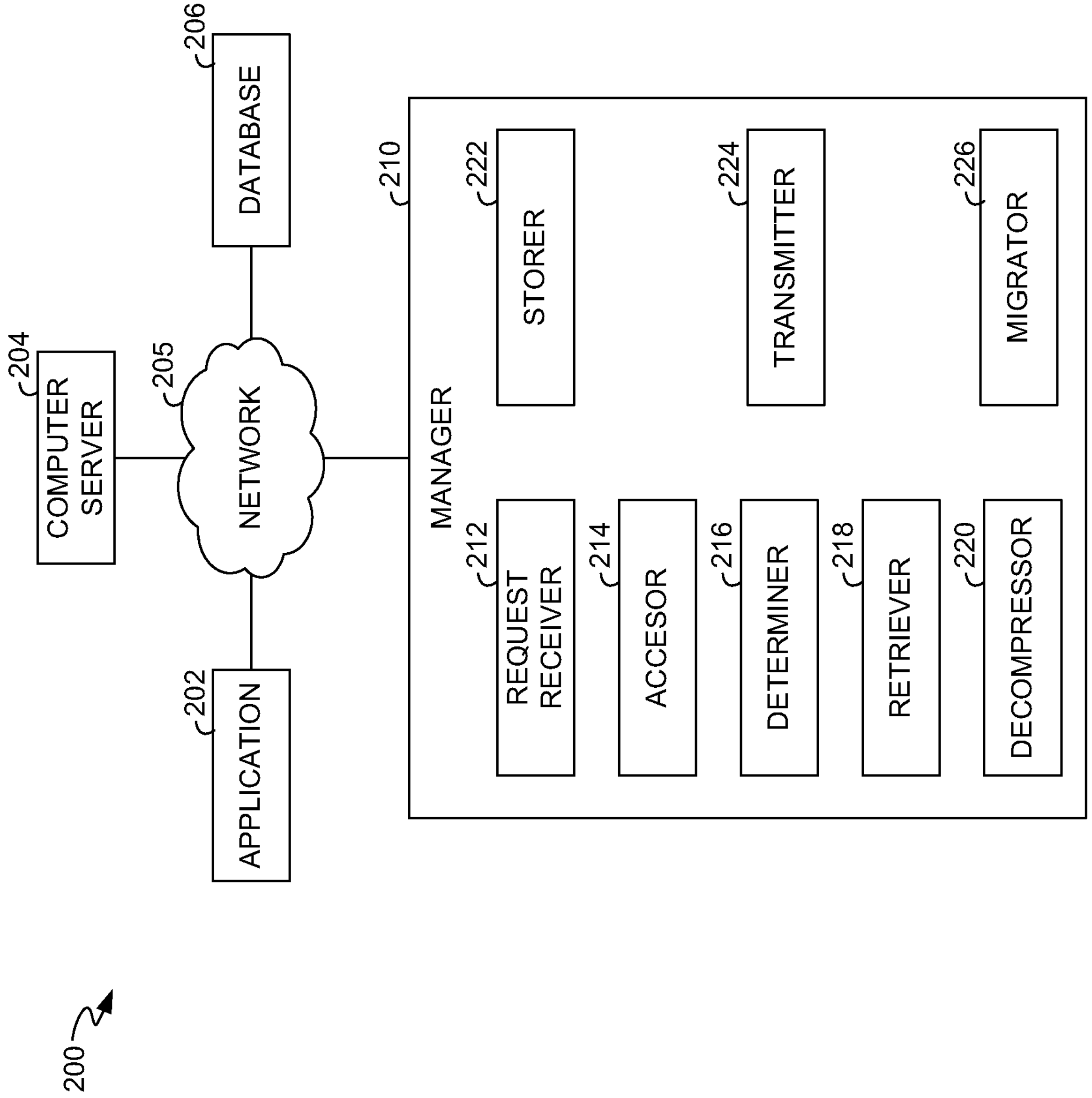
FIG. 2 is an example system architecture suitable to implement embodiments of the present invention.

Turning now to FIG. 2, an exemplary computing system 200 is depicted. The computing system 200 (hereinafter "system") is merely an example of one suitable computing system and is not intended to suggest any limitation as to the scope of use or functionality of embodiments of the present invention. Neither should the system 200 be interpreted as having any dependency or requirement related to any single component or combination of components illustrated herein.

In some embodiments, one or more of the illustrated components may be implemented as a stand-alone application. The components described are exemplary in nature and in number and should not be construed as limiting. Any number of components may be employed to achieve the desired functionality within the scope of the embodiments hereof. Further, components may be located on any number of servers.

In the embodiment shown in FIG. 2, the system 200 includes an application 202, a computer server 204, a network 205, a database 206, and a manager 210. While FIG. 2 illustrates only one application 202, one database 206, and one computer server 205, it is contemplated that the system 200 may comprise any number of applications 202, databases 206, and servers 205.

In aspects, the application 202 is utilized by a healthcare provider to request and view the medical images. It is contemplated that the application may be a standalone application for viewing medical images or may be a part of a larger electronic medical record (EMR) application. Additionally, the application 202 may be accessed from multiple difference sources including, but not limited to, a desktop, laptop, tablet, or cellphone. As such, the application 202 can communicate a request to view images from a healthcare provider to the system 200 via network 205. Upon finding and processing the image data for the medical image requested, the system will then transmit the medical image to the application 202 for viewing. The application 202 may also present additional information to the healthcare provider. For example, if the application is a part of the EMR being utilized by a healthcare system, the application 202 may also access and present information found in the electronic medical record, such as biographical information, prior medical history, assessment information for the individual, and any other pertinent medical data monitored by a healthcare system.

Generally, the manager 210 is configured to manage requests received for medical images, locate and retrieve the medical image data, process the medical image data, and provide the medical image for viewing. In this embodiment, the manager 210 is comprised of a request receiver 212, accessor 214, determiner 216, retriever 218, decompressor 220, storer 222, transmitter 224, and migrator 226. In this aspect, the manager 210 is comprised of eight subcomponents (listed above). However, in other aspects, the manager 210 may be comprised of more or less components and any and all variations are contemplated herein. The components described are exemplary in nature and in number and should not be construed as limited. Any number of components may employed to achieve the desired functionality within the scope of the embodiments hereof.

Additionally, in some aspects, the manager may also be located within the database 206. It will be appreciated that some or all of the subcomponents of the manager 210 may be accessed via the network 205 and may reside on one or more devices. Further, while system 200 is comprised of one manager 210, it is contemplated that the system 200 may include more than one manager 210. It is also contemplated that the manager 210 may be integrated into the application 202.

The request receiver 212 within the manager 210 is configured to receive a first request from a first user to view a first medical image comprising medical image data that includes at least one image frame. The request receiver 212 may receive the first request from the first user via an application such as application 202 which may be utilized on the first user's interface (e.g. desktop, laptop, mobile device, tablet, etc.) The request received by the request receiver 212 may be received from a user at a facility, such as a hospital. In some instances, the request may be received from a user working remotely from another location outside the facility. It is contemplated that the request receiver 212 can receive a request via any device connected to the network 205.

Additionally, the request receiver 212 is not limited to receiving requests from only the first user. It is contemplated that the request receiver 212 may receiver more than one request from the first user and further may receive one or more requests from additional users. The request receiver 212 may receive the request to review medical images from a variety of individuals including, but not limited to, a healthcare provider, such as a radiologist, who needs to review one or more medical images for one or more individuals and prepare assessments and diagnoses. When a user requests the first medical image, the user may be utilizing an application, such as application 202, to view medical image data. For example, a radiologist may use a Picture Archiving Communication Systems (PACS) to view the images. While the disclosure describes a first user requesting a first medical image and a second user requesting a second medical image, it is contemplated that the first user may request more than one medical image for viewing at the same time or sequentially and that there may be any number of users utilizing the system 200 to review medical images.

Next, the accessor 214 accesses a least recently used (LRU) memory cache to determine whether the medical image data requested by the first user is stored in the LRU memory cache. Systems, such as system 200, comprise LRU memory cache that temporarily stores data. In this case, the LRU memory cache is configured to store recently used data. Storing data in a LRU memory cache provides a very fast way to retrieve data compared to retrieving data from other memory or storage. However, while the LRU memory cache provides quick retrieval, the amount of data that can be stored in the LRU memory cache is limited. As such, only a small percentage of data may be stored in the LRU memory cache. Therefore, then the LRU memory cache reaches its storage limits, the least recently used data will be removed to free up space for new data. For example, once a healthcare provider is finished reviewing the first medical image, they may request viewing a second, third, and fourth medical image. Because of the size of the image data files, the LRU memory cache may be limited to storing only 3 medical images at a time. Therefore, once the medical image data for the second, third, and fourth images have been located, retrieved, and processed for viewing, the medical image data corresponding to the first medical image may be removed to free up space for the second, third, and fourth medical images' data. The medical image data for the first image may be moved to another local storage location, such as a local database or may be migrated to a remote storage location. Further processing may take place on the medical image data in order to store it in another location.

In some aspects, the accessor 214 will access the LRU memory cache and determiner 216 will determine that the medical image data is stored in the LRU memory cache. If this occurs, then the retriever 218 will retrieve the requested medical image data from the LRU memory cache and transmit it to the first user via the transmitter 224. Generally, medical image data that is stored in the LRU memory cache will have already been processed and stored in a decompressed format. Therefore, the system 200 may not need to perform additional processing on the medical image data and the transmitter 224 can transmit the medical image data for the first medical image to the first user for review without taking additional time to perform any processing.

Because the LRU memory cache is limited in storage space, larger medical image data files and files not currently being used, will be stored elsewhere. As such, in other instances, the accessor 214 will access the LRU memory cache and the determiner 216 will determine that the requested medical image data is not present in the LRU memory cache. When this occurs, the accessor 214 will then access a second potential storage location, a local database, such as database 206. The local database will be able to store a larger amount of data than the LRU memory cache and as such, more medical image data files can be stored there. If the determiner 216 determines that the medical image data is present in the local database, then the retriever 218 will retrieve the medical image data and the transmitter 224 will transmit such data to the first user. The system 200 may store the medical image data at the local database in a decompressed format, making it ready for use upon request with little to no additional processing. In other instances, it is contemplated that additional processing may be required to configure the medical image data in a format for use by the first user.

By contrast, if the determiner 216 determines that the requested medical image data file is not present in the local database, then the accessor 214 will access a remote image storage. The remote image storage is located remotely and has a greater storage capacity then both the LRU memory cache and local database. The determiner 216 will determine the presence of the requested medical image data in the remote image storage and locate the medical image data. Then, the retriever 218 will retrieve the medical image data. Upon retrieving the data, the decompressor 220 will separate the medical image data comprising the plurality of image frames into pixel data and metadata. Then the decompressor 220 will perform decompression on the pixel data and the metadata for each of the plurality of image frames. By decompressing the data, the medical image data can then be stored locally at either the LRU memory cache or the local database for future use. This allows the system 200 to increase the speed of retrieval upon future request for the medical image since the medical image data has already been decompressed and can be quickly and easily retrieved and then transmitted to the user. The storer 222 will store the decompressed medical image data in either the LRU memory cache or the local database depending on the size of the medical image data and availability of space in both locations. Smaller files, or those with fewer image frames and less complex images, are more likely to be stored in the LRU memory cache. Other medical image data that comprises larger amounts of data (e.g. hundreds of image frames) may be stored in the local database.

In either instance, the decompression by the decompressor 220 and storage by storer 222 of the decompressed medical image data enables faster, more efficient retrieval upon a future request. As mentioned, the request receiver 212 may receive more than one request for medical images from the first user or a subsequent second user. For example, the request receiver 212 can receive a second request for the medical image previously requested by the first user in the first request. When this occurs, the accessor 214 will first access the LRU memory cache to determine, via determiner 216, whether the medical image data for the medical image requested has been stored in the LRU memory cache. If the determiner 216 determines that the requested medical image data has been stored in the LRU memory cache, then the transmitter 224 will transmit the requested medical image data to the second user for viewing. However, if the determiner 216 determines that the medical image data requested is not stored in the LRU memory cache, then the accessor 214 will access the local database and locate the requested medical image data. Once located, the retriever 218 will retrieve the medical image data and the transmitter 224 will transmit the medical image data for the first image to the second user, via the second user's interface, for viewing. As noted, because the medical image data stored locally at either the LRU memory cache or the local database was previously decompressed in response to the first request for the medical image data, the time to respond to the second request will be significantly less than the first request. The accessor 214 will only need to access the local storage at the LRU memory cache or local database, which will be faster and more efficient than accessing a remote storage, such as the remote image storage. Therefore, the transmission of the medical image data by the transmitter 224 in response to the second request will occur at a higher framer rate than the transmission of the medical image data to the first request. By storing the recently requested medical image data locally, the system will save time, and cost associated with accessing remote storage and then decompressing the data.

Additionally, it should be noted that while the accessor may first access the LRU memory cache to determine whether the previously decompressed medical image data for the medical image requested was stored in the LRU memory cache and based on that determination by the determiner 216, access the local database, it is also contemplated that the accessor 214 can be configured to access the local database prior to the LRU memory cache or both the LRU memory cache and the local database at the same time. Once the determiner 216 has determined the location of the requested medical image data in either the LRU memory cache or the local database, the transmitter 224 will transmit the previously compressed medical image data to the second user in response to the second request. The second user can then view the medical image on the second user's interface.

While this example describes the same medical image data being requested by the second user, any number of users may request the same medical image as the first user or different medical images for viewing. If the medical image data requested in the second request is not the same medical image data as the first request, then the system 200 will initiate the steps described above to locate the medical image data, retrieve the medical image data, decompress the medical image data, transmit the data to the user, and then store the medical image data locally at the LRU memory cache or the local database. Depending on the availability of space for storing the new medical image data locally, the system may move the first medical image data from the LRU memory cache or the local database to a remote location in order to store the new medical image data locally at the LRU memory cache or local database. The LRU memory cache and the local database may store medical image data from more than one request. Depending on the sizes of the medical image data files requested, there may be as few as one medical image data file in the LRU memory cache or as many as hundreds of medical image data files.

Once the medical image data has been decompressed and stored in either the LRU memory cache or the local database, the medical image data will remain there until the system receives an indication that the medical image data is no longer needed. This indication may come directly from a user that had requested the medical image data. Additionally, the indication may come from a user closing a viewing application used to review the medical image data transmitted. These methods of communicating to the system that the medical image data is no longer needed are merely examples and any and all variations of communication pathways between the user and the system are contemplated herein. In other instances, the system 200 may receive an indication to move the medical image data for the first medical image to remote storage to make room for a subsequently requested medical image and its associated medical image data.

Upon receiving the indication that that the medical image data is no longer in use or that the local storage at the LRU memory cache or local database needs space for other medical images requested after the first medical image, the migrator 226 will migrate the medical image data to the remote image storage. For example, the second user may complete the review of the medical image data requested and either send a signal that the review is complete or close the viewing application. When this occurs, the medical image data is no longer needed. Because the LRU memory cache and local database are limited in storage space, once the medical image data review is complete, the migrator 226 can move the medical image data back to the remote image storage. This will free up valuable space in the LRU memory cache and local database for responding to future requests for other medical image data from users.

While the LRU memory cache storage size is more limited than the local database, the storage size can be dynamically modified to store all image frames for a particular medical image. For example, if an ultrasound image data file size is very large (e.g., 1000 image frames) but the LRU memory cache current storage capacity is for 700 image frames, the system can dynamically modify the size of the LRU memory cache in order to store all 1000 of the ultrasound image frames at a high frame rate. While the system 200 can dynamically modify the size of the LRU memory cache, it will be restricted by the available RAM on a device being used to view the medical images (e.g. tablet, laptop, cell phone). Therefore, the LRU memory cache storage space limitations can vary based on the device used to view the medical image requested. Additionally, the LRU memory cache can also be modified to decrease the storage capacity if the system 200 determines a need to make RAM available for another application on the system 200. The system 200 can compute the amount of RAM available and the amount of RAM required for each decompressed image frame before decompression occurs, and as a result dynamically modify the size of the LRU memory cache accordingly.

In some instances, it is contemplated that the accessor 214 may be capable of accessing all three potential storage locations of medical image data at the same time. For example, upon the request receiver 212 receiving a request for medical image data, the accessor 214 may be configured to simultaneously access the LRU memory cache, local database, and remote image storage to determine the location of the medical image data that has been requested. In this case, the system would further decrease the response time to the request since the system 200 will be able to access all three potential storage locations at the same time, decreasing the time it takes to determine the location of the medical image data and retrieve such data. If the determiner 216 determines that the medical image data is located on the remote image store, then the retriever 218 will retrieve the medical image data from the remote image store in the compressed format. Upon retrieving the data, the decompressor will decompress the medical image data so that it can be stored more efficiently and transmitted for viewing by the transmitter 224. The storer 22 will store the decompressed medical image data in either the LRU memory cache or the local database, depending on the size of the medical image data (e.g. how many image frames are present). The transmitter 224 will transmit the decompressed medical image data to the first user for review. Subsequently, the request receiver 212 may receive a second request for the same medical image data from a second user. For example, the first user might be a radiologist who requests the medical image data to review the radiological images (e.g. CT scan of the brain) to make a diagnosis. Then, a neurologist, may initiate a second request to also view the images. Since the previously decompressed medical image data of the CT scan of the brain would have been stored locally at either the LRU memory cache or the local database, the system will be able to respond quicker to the second request from the neurologist. No additional processing will be needed on the medical image data since the medical image data was already decompressed by the decompressor 220. With the medical image data in decompressed format and ready for transmission, the transmitter 224 will be able to transmit the medical image data to the neurologist for review much quicker. As noted, by storing the medical image data locally and in a decompressed format, the system 200 is able to respond to medical image request much faster and more efficiently. This will lead to a significant decrease in cost, and allow healthcare providers to retrieve radiological images much faster for review and diagnosis, which may be critical to saving lives.

Once again, the system 200 will receive an indication that the medical image data is no longer needed. In some instances, the indication may be received from an image viewing application that is used by the healthcare provider to review the medical image data. In other instances, it is contemplated that the indication may come from the input of certain data into an EMR. For example, upon determining a diagnosis and treatment plan and inputting the information into the EMR, the healthcare provider may either save or update the information added to the EMR and then close that patient's individual chart within the EMR. This closing of the chart may indicate to the system 200 that the medical image data is no longer needed and then the migrator 226 can migrate the medical image data back to a remote storage location, such as the remote image storage. This will free up space in the local storage locations for additional future requests.

In other instances, the medical image data can remain in the local storage at either the LRU memory cache or local database until additional medical image data files are requested by a subsequent user. For example, even if the first and second user are done with the review of the medical image data, the decompressed medical image data can remain in the LRU memory cache or the local database until the request receiver 212 receives a request for a different set of medical image data. Further, it is contemplated that medical image data stored in the LRU memory cache can be migrated from the LRU memory cache to the local database for storage prior to any migration to the remote image storage since the local database has more storage space than the LRU memory cache. In other instances, the medical image data may be kept in the LRU memory cache or the local database for a predetermined period or until some other triggering event occurs. The continued storage of decompressed medical image data locally at the LRU memory cache and local database will depend on a variety of factors and is not limited to those explicitly described herein.

It should also be noted that when the request receiver 212 receives the request for a medical image, the medical image a requested will contain some sort of identification information. For example, each image frame within the medical image data may be assigned a unique identification number and each medical image data file may also be assigned a unique identification number. As such, when a user requests the medical image, the request receiver 212 will receive identifying information for the medical image requested and the components of the manager 210 will all utilize the identifying information in order to access, retrieve, decompress, store, transmit, and migrate the medical image data.

It is further contemplated that the request receiver 212 may receive requests for the same medical image data from users at different locations. For example, a radiologist remotely connected to the network 205 of a healthcare system may request to view a medical image data from one location while an emergency department physician may request the same medical image data for review from a different location within the healthcare system. In some aspects, the system 200 will receive requests from more than one user at either the same or a different facilities within the shared network.

Figure 3:
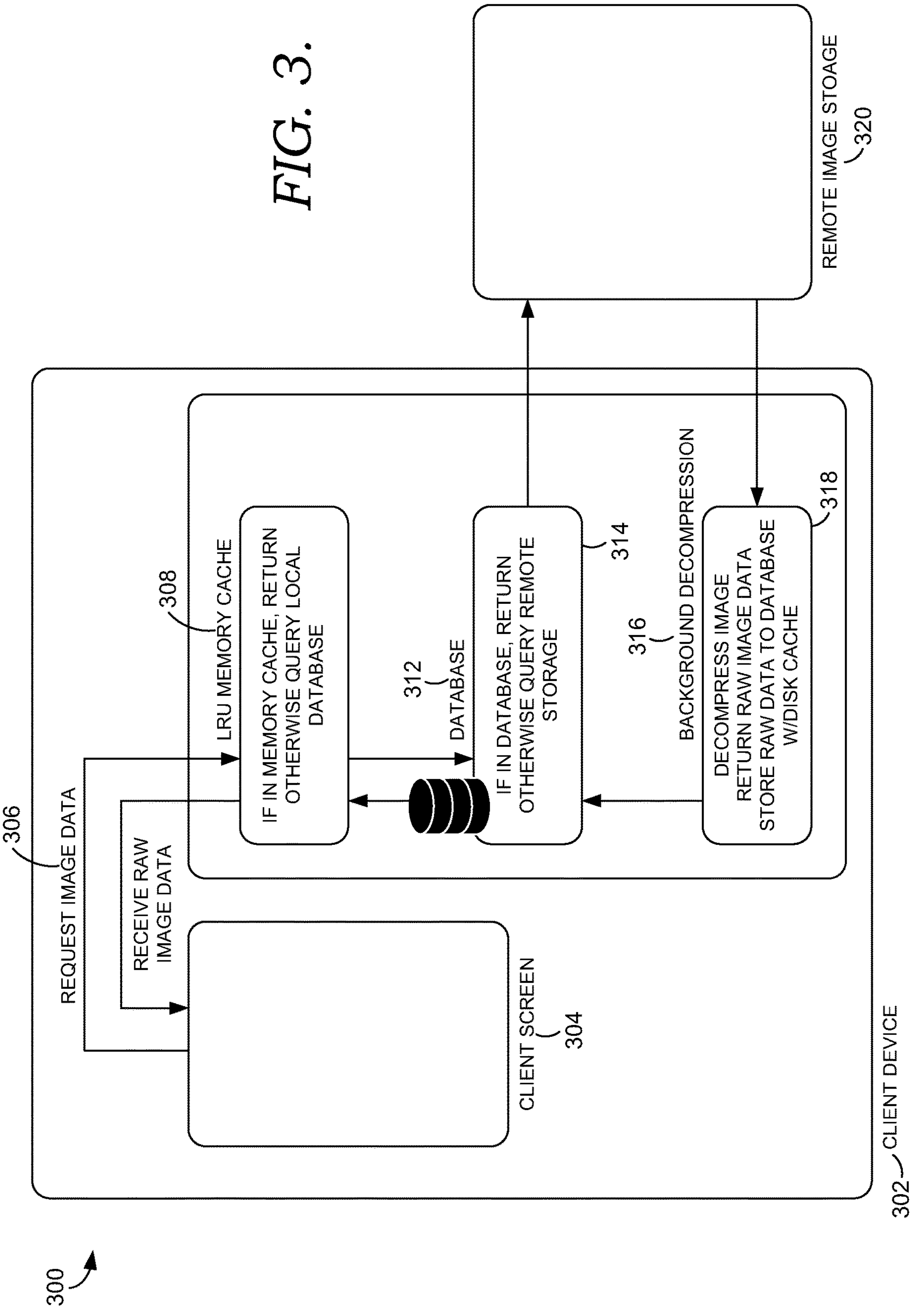
FIG. 3 illustrates an example system workflow illustrating implementation of embodiments of the present application.

Turning next to FIG. 3, an exemplary system workflow 300 of utilizing a dynamic multi-layer caching system 200 for providing fast diagnostic image renderings is illustrated. The process begins at a client screen 304 located on a client device 302. The client screen might be located on a desktop, laptop, cell phone, or any device capable of connecting to the specific healthcare network, such as network 205 of FIG. 2. The example client, a radiologist, requests medical image data at 306. This request may come through an image viewing application, such as a PACS, or via the EMR, or any application that is authorized to communicate with the system 200. Upon receiving the request to review a medical image, the accessor 214 will access the LRU memory cache at 308. If the determiner determines that the requested medical image is in the LRU memory cache, then the transmitter 224 will transmit the requested medical image to the client screen 304. When the medical image is transmitted it will be transmitted in raw form or decompressed. As such, if the medical image data has not been decompressed, the decompressor 220 will need to decompress the data to be transmitted for viewing.

If the determiner 216 determines that the medical image data requested is not located in the LRU memory cache, then the accessor 214 will access the local database at 312. As shown in FIG. 3, the local database and LRU memory cache are both located on the client device. In other words, any medical image data that is stored in the LRU memory cache or local database may be stored locally on the client device 302, making the medical image data readily available for access upon request. As mentioned, the medical image data that is stored in both the LRU memory cache and local database is preferred to be in the decompressed state, but it is possible that the medical image data may also be stored in the compressed format. However, to minimize computation and processing time, it is important that the medical image data that is stored at either the LRU memory cache or the local database is stored in the decompressed format. If stored in the compressed format, the medical image data will need to undergo decompression prior to transmission, which will decrease the speed that a requested medical image is transmitted for viewing. If the determiner 216 determines that the requested medical image data is located at the local database, then the transmitter will transmit the medical image data to the client screen 304 for review. Once again, prior to transmitting the medical image, the decompressor 220 will decompress the medical image data if it was not already decompressed. Then, the medical image will be transmitted, via the transmitter 224, for viewing on the client screen 304.

When the determiner 216 determines that the medical image data requested is not present on the LRU memory cache or the local database, the determiner will then query the remote image storage 320, which FIG. 3 illustrates as not being located within the client device 302. Once the retriever 218 retrieves the medical image data requested from the remote image storage 320, the decompressor will decompress the medical image data to raw data for storage either in the LRU memory cache or the local database at 318. As previously discussed, once the medical image data has been decompressed, the medical image data will be transmitted by the transmitter 224 to the client screen 304. It is also noted that prior to transmitting the decompressed medical image for viewing on the client screen 304, the decompressor may complete additional final processing on the data so that the medical image data is optimized for viewing and analysis.

By storing the decompressed medical image data in the LRU memory cache and local database, minimal operations are needed to take place when the medical image is requested after the initial request. Additionally, the dual layer of caching in either the LRU memory cache or the local database allows the system to achieve the fastest frame rate possible, which provides the image to the user faster. The amount of time it will take for the system to respond to the request is dependent on the network environment and how large the medical image data file is. However, it is contemplated that the entire process may take between 1-900 milliseconds. As discussed, the present system is beneficial as it eliminates the amount of processing required in responding to a request to view medical image data. It also provides for the storage of decompressed medical image data for requested medical images locally, which is more efficient. It is further noted that the system 200 may transmit the medical image data for viewing at the same time that the medical image data is stored in either the LRU memory cache or the local database. Further, in aspects, the decompressed medical image data might be cached after the medical image data is transmitted to the user for viewing.

Figure 4:
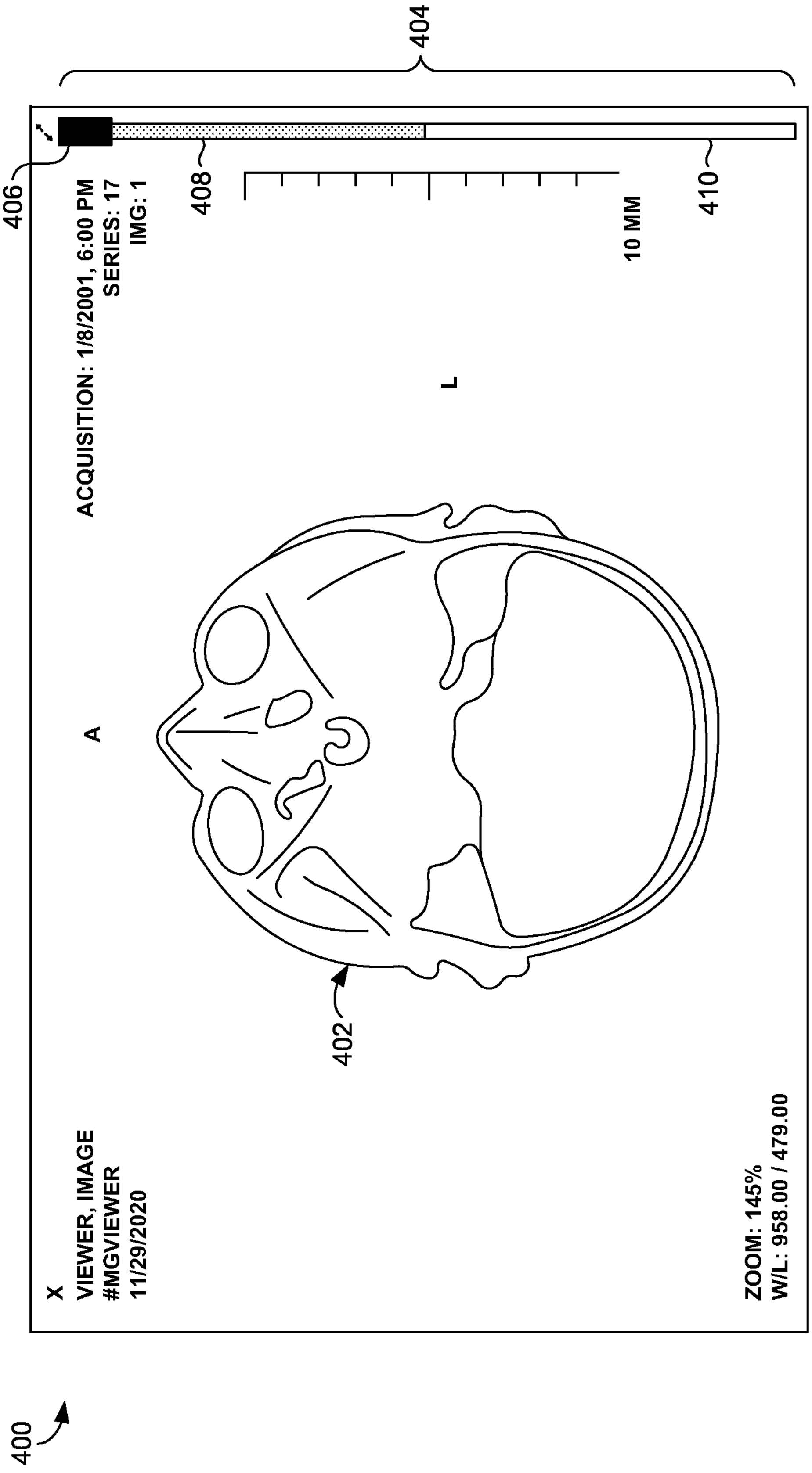
FIG. 4 illustrates an example medical image frame generated for viewing in response to a request by a first user.
Figure 5:
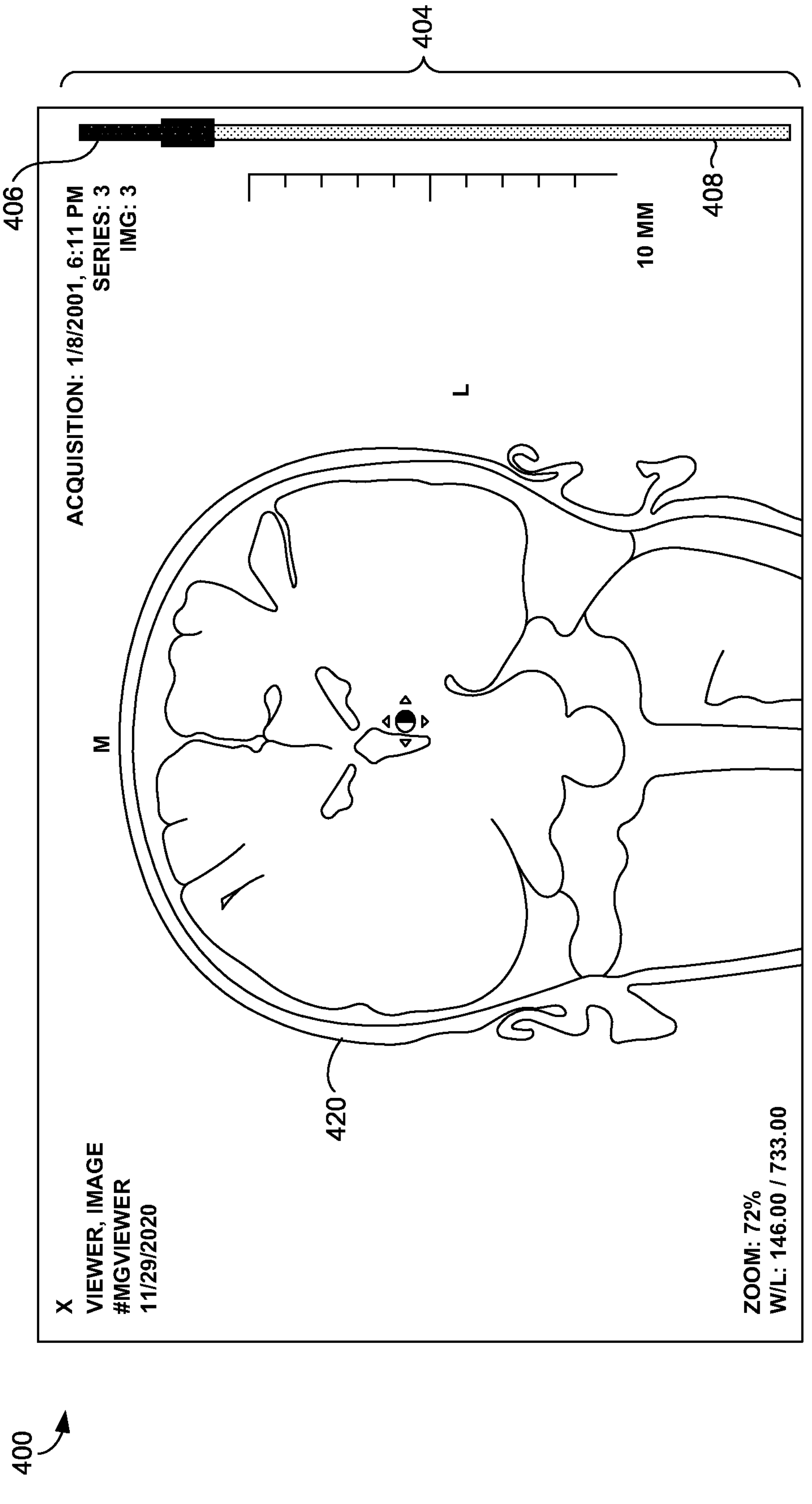
FIG. 5 illustrates another example medical image frame generated for viewing in response to a request by the first user.

Turning to FIGS. 4 and 5, example image frames from decompressed medical image data are illustrated. The example illustrations are radiological images of the brain. As shown in radiological image 400, a top down view of the brain and its structures are illustrated. This image 400 is a single frame that might be a part of a series of hundreds of image frames from a radiological exam conducted on a patient. On the right hand side of the image of FIGS. 4 and 5, a scroll bar 404 is depicted that illustrates a plurality of image frames corresponding to medical image data to be transmitted for viewing. The scroll bar 404 is used by a user to navigate through various image frames for the requested medical image data. As such, FIG. 4 illustrates a first image frame in which the top of the brain is shown while the image in FIG. 5 illustrates a second image frame in which the rear portion of the brain, including the brain stem are shown. The images depicted in FIGS. 4 and 5 are only used for exemplary purposes and may not be sequential image frames.

The scroll bar 404 is shown comprising three sections 406, 408 and 410. In FIG. 4, the blacked out section that comprises section 406 represents the image frames behind the current image that have already been downloaded and the section 408 illustrates the image frames in front of the current image frame that are being downloaded. Section 410 illustrates those image frames which have not been retrieved and decompressed. The image frames in section 410 may be those frames that are not stored locally and will be retrieved by retriever 218 from the remote image storage. Then the decompressor will need to decompress the medical image data for the frames in section 410 prior to transmitting the image frames for viewing. Those images that have already been downloaded are the medical image data that had been stored locally at the either the LRU memory cache or the local database. As such, the medical image data for the image frames in section 406 were already decompressed by the decompressor 220 and ready for transmission by transmitter 224 for viewing on the user's screen. Therefore, when a user is viewing the image frames in section 406, the images will load very quickly since little to no processing is needed on the medical image data and the data has already been decompressed into raw format for transmission and is stored locally. Therefore, upon request, the image data that has already been processed and stored in the LRU memory cache or local database can be retrieved almost instantaneously and displayed on the user's screen.

As the user scrolls through the series of image frames and arrives at image frame 420, the system 200 has continued to retrieve the remaining series of image frames associated with the requested medical image data. This is illustrated in FIG. 5 as the portion of the scroll bar shaded comprising section 406 has grown larger, indicating that the system 200 has completed retrieval of more of the image frames for viewing. Additionally, the system 200 is actively retrieving the remaining image frames for the requested medical image data in section 408. As such, section 410 has been eliminated. As the retrieved image frames increase, section 406 will continue to take over the scroll bar 404 until all image frames for the requested medical image have been retrieved, decompressed, and transmitted for viewing. When this occurs, the entire scroll bar 404 will compose of only the shaded in portion of section 406. While not shown, as the user scrolls through the image frames, those that are already decompressed and stored locally will appear faster and as such, when the user is scrolling they will be able to go through the locally stored image frames faster than those image frames that are being retrieved and decompressed. Additionally, the image frames that might be stored in the LRU memory cache will be loaded faster than those images in the local database.

Because often times the medical image data requested may include hundreds to thousands of image frames (e.g. CT scan or MRIs), when the medical image data is initially saved, it is often separated into multiple series. As such, as a radiologist might be reviewing series of images corresponding to a CT scan, all of the hundreds or thousands of image frames may not be able to be stored in the decompressed format locally. As such, as the radiologist scrolls through the image frames that have been retrieved and already viewed (e.g. section 406) may be migrated from the LRU memory cache by migrator 226 to the local database and the currently viewed image frames may be stored in the LRU memory cache.

Figure 6:
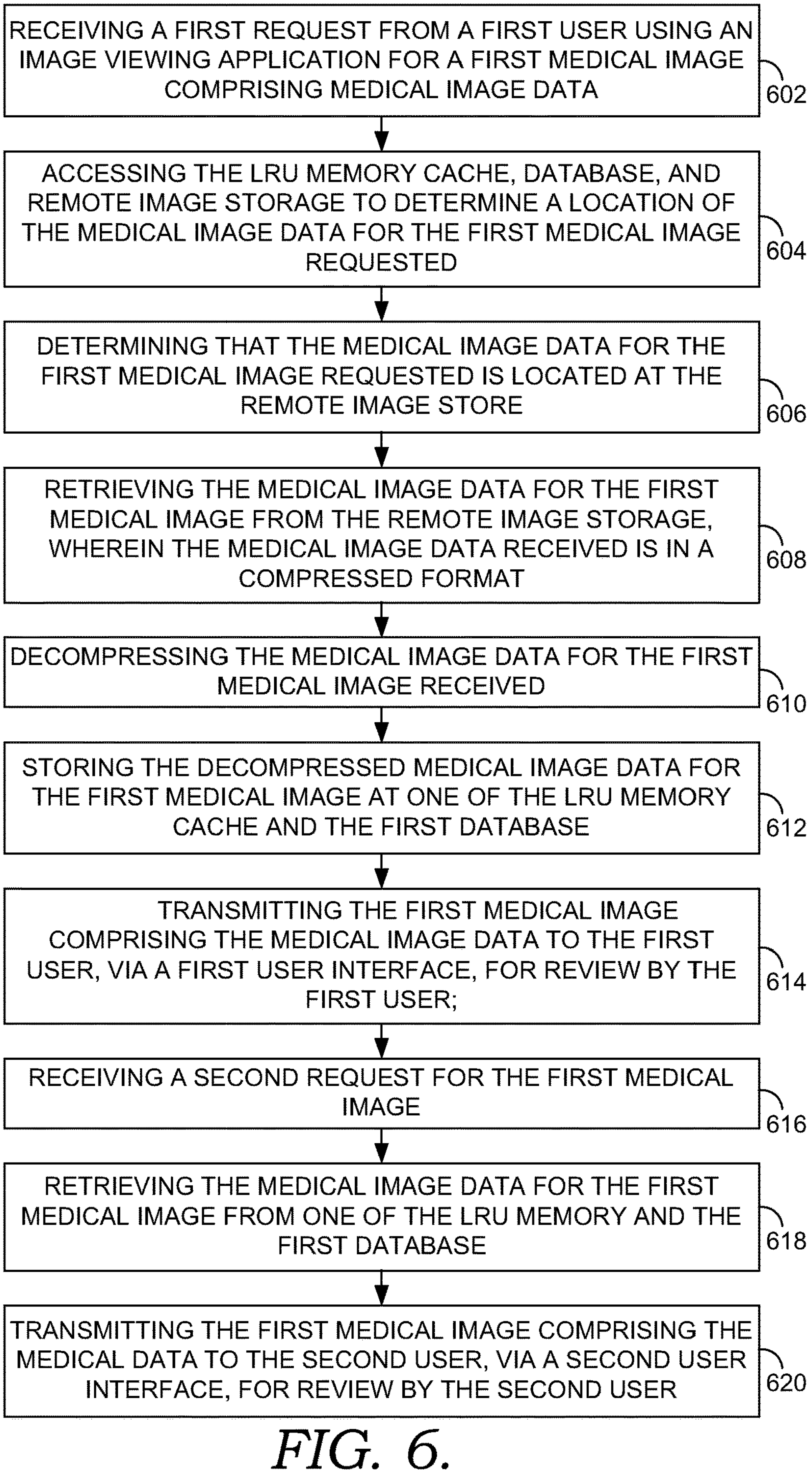
FIG. 6 is a flow diagram descripting an exemplary method of executing embodiments of the present invention.

FIG. 6 illustrates a flow diagram showing an exemplary method 600 of executing embodiments of the present disclosure. Beginning with block 602, the request receiver 212 receives a first request from a first user using an image viewing application for a first medical image comprising medical image data. Then, at block 604, the accessor 214, accesses the LRU memory cache (e.g., a first storage device in a sequence) to determine whether the medical image data for the first medical image is stored in the LRU memory cache. After determining that the medical image data is not stored in the LRU memory cache, the accessor 214 accesses the local database (e.g., a second storage device in the sequence) to determine whether the requested medical image data is stored in the local database. After determining that the medical image data is not stored in the local database, the accessor 214 will access the remote image storage (e.g., a third storage device in the sequence). Then, at block 606, the determiner 216 will determine that the medical image data requested is located at the remote image storage. The retriever 218 will then retrieve the medical data image from the remote image storage in a compressed format at block 608. Then, the decompressor 220 will decompress the medical image data into raw data for storing and transmission at block 610. The storer 222 will store the decompressed medical image data in either the LRU memory cache or the local database depending on the size of the medical image data and other system demands at block 612. The transmitter 224 will transmit the raw, decompressed medical image data for the first medical image to the first user, via the first user's interface at block 614. If no additional requests are received and the first user indicates that the review of the medical image data has been completed, the system may keep the decompressed medical image data stored locally at the LRU memory cache or local database if adequate storage space is available. In other instances, the migrator will migrate the medical image data back to the remote image storage.

In instances where the request receiver 212 receives a second request for the medical image data for the first medical image at block 616, the accessor 214 will access the LRU memory cache and/or the local database in order to retrieve the medical image data that has been stored locally at step 618. The medical image data that is in decompressed format and had been stored locally will then be transmitted to the second user, via the second user's interface, for review at block 620.

While not shown in FIG. 6, after the second user has completed review of the medical image, the system may receive an indication that review of the medical image is finished. Based upon other requests and storage availability, the system can allow the medical image data to remain stored locally at either the LRU memory cache or the local database. The system may first store the medical image data at the LRU memory cache and then migrate it to the local database as the LRU memory cache storage space may be needed to store other image data. As more and more data is requested, the migrator 226 can migrate the medical image data from the local database back to the remote image storage. The medical image data may be compressed prior to migrating to the remote image storage. It is also contemplated that the medical image data might remain in raw, decompressed format and migrated to the remote image storage.

While block 602-620 present the method in order discussed above, it is contemplated that the system 200 may receive the indications and requests from the first user at the and the second user simultaneously. As such, the system 200 may provide the both the first user and the second users with the medical images for review by each user simultaneously. System 200 is adaptable and intelligent and as such, the presented method is exemplary and variations in the order are contemplated herein.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A dynamic multi-layer caching system useful for providing fast diagnostic image renderings to a healthcare provider for viewing of one or more medical images, the system comprising one or more processors configured to:

receive a first request from a first user to view a first medical image comprising medical image data, wherein the medical image data comprises at least one image frame;

access a least recently used (LRU) memory cache to determine whether the first medical image is stored in the LRU memory cache;

determine that the first medical image is not stored in the LRU memory cache in response to the first medical image not being located in the LRU memory cache;

upon determining that the first medical image is not stored in the LRU memory cache, access a local database to determine whether the first medical image is stored in the local database;

determine that the first medical image is not stored in the local database in response to the first medical image not being located in the local database;

upon determining that the first medical image is not stored in the local database, access a remote image storage;

determine that the first medical image is located on the remote image storage;

retrieve the first medical image from the remote image storage;

decompress the medical image data for the first medical image;

transmit the first medical image comprising the decompressed medical image data to the first user, via a first user interface, for review by the first user; and store the decompressed medical image data at one of the LRU memory cache and the local database for future requests for the first medical image.

2. The system of claim 1, wherein the system is further configured to receive a second request for the first medical image from a second user.

3. The system of claim 2, wherein the system is further configured to access one of the LRU memory cache and the remote image storage to retrieve the first medical image in response to the second request.

4. The system of claim 3, wherein the system is further configured to transmit the previously decompressed medical image data to the second user.

5. The system of claim 4, wherein a transmission, by the system, of the medical image data in response to the second request is faster than a transmission by the system, of the medical image data in response to the first request.

6. The system of claim 5, wherein the transmission of the medical image data in response to the second request occurs at a higher frame rate than the transmission of the medical image data in response to the first request.

7. The system of claim 6, wherein the system is further configured to receive an indication that the second user has completed reviewing the medical image data.

8. The system of claim 7, wherein, in response to the indication that the second user has completed reviewing the medical image data, the system is configured to migrate the medical image data from one of the LRU memory cache and the local database to the remote image storage.

9. The system of claim 1, wherein the system is further configured to dynamically modify a storage capacity of the LRU memory cache based determining an amount of available RAM and an amount of RAM required for each image frame comprising the medical image data.

10. The system of claim 1, wherein the medical image data transmitted to the first user is displayed as one or more radiological images.

11. The system of claim 1, wherein the medical image data of the first medical image is separated, the separation of the medical image data comprises separating pixel data from metadata for each image frame.

12. The system of claim 1, wherein the medical image data requested comprises a series of radiological images.

13. A dynamic multi-layer caching system useful for providing diagnostic image renderings to a healthcare provider for viewing of one or more medical images, the system comprising:

a least recently used (LRU) memory cache;

a local database comprising a disk cache;

a remote image storage;

an application;

one or more processors; and a storage device storing a computer program product comprising computer instructions that, upon execution by the one or more processors, cause the one or more processors to perform operations comprising:

receiving a first request from a first user, via an application, for a first medical image comprising medical image data;

in response to the first request, accessing each of the LRU memory cache, the local database, and the remote image storage to determine a location of the medical image data for the first medical image requested, wherein the accessing comprises:

accessing the LRU memory cache, the local database, and the remote image storage in sequence in response to the first medical image not being located in the LRU memory cache and the local database until the first medical image is located in the remote image storage;

in response to the first medical image being located in the remote image storage, retrieving the medical image data for the first medical image from the remote image storage, wherein the medical image data retrieved is in a compressed format;

decompressing the retrieved medical image data for the first medical image received;

after the decompressing, transmitting the decompressed medical image data for the first medical image to the first user, via a first user interface, for review by the first user;

storing the decompressed medical image data for the first medical image at one of the LRU memory cache and the local database in which the first medical image was not located;

receiving a second request for the first medical image from a second user;

accessing and retrieving the medical image data for the first medical image from one of the LRU memory cache and the local database; and transmitting the first medical image to the second user, via a second user interface, for review by the second user.

14. The system of claim 13, wherein the system is further configured to receive a communication from the application that the first medical image is no longer needed.

15. The system of claim 14, wherein the system is further configured to migrate the first medical image to the remote image storage in response to receiving the communication that the first medical image is no longer needed.

16. The system of claim 13, wherein the local database comprises more storage space for storing the first medical image than the LRU memory cache.

17. The system of claim 13, wherein the first medical image comprises at least one image frame.

18. The system of claim 13, wherein the system is further configured to determine the location of the first medical image based on an assignment of an identification number to the first medical image.

19. A method carried out by a server to utilize a dynamic multi-layer caching system useful for providing diagnostic image renderings to a healthcare provider for viewing of one or more medical images, the method comprising:

receiving a first request from a first user using an image viewing application for a first medical image comprising medical image data;

in response to the first request, accessing a plurality of storage devices in sequence in response to not locating the first medical image in one or more of the plurality of storage devices including a LRU memory cache, a local database, and a remote image storage to determine a location of the first medical image requested;

in response to the first medical image being located in the remote image storage, retrieving the medical image data for the first medical image from the remote image storage, wherein the medical image data retrieved is in a compressed format;

decompressing the retrieved medical image data for the first medical image received;

after the decompressing, transmitting the first medical image comprising the decompressed medical image data to the first user, via a first user interface, for review by the first user;

after the transmitting, storing the decompressed medical image data for the first medical image at one of the LRU memory cache and the local database in which the first medical image was not located to be available for a second request;

receiving the second request, subsequent to the first request, to view the first medical image from a second user;

retrieving the first medical image from one of the LRU memory cache and the local database; and transmitting the first medical image comprising the decompressed medical image data, via a second user interface, for review by the second user.

20. The method of claim 19, further comprising migrating the first medical image to the remote image storage in response to receiving a communication that the first medical image is no longer needed.

* * * * *